United States Patent
Fearnhead et al.

(10) Patent No.: US 6,670,139 B1
(45) Date of Patent: *Dec. 30, 2003

(54) CELL-FREE ASSAY USING ONCOGENE-INDUCED APOPTOSIS TO IDENTIFY INHIBITORS OF APOPTOSIS IN DRUG-RESISTANT CELLS

(75) Inventors: Howard O. Fearnhead, Huntington Station, NY (US); Mila Elena McCurrach, Cold Spring Harbor, NY (US); Scott William Lowe, Cold Spring Harbor, NY (US); Yuri Lazebnik, East Norwich, CT (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/235,738

(22) Filed: Jan. 22, 1999

Related U.S. Application Data

(62) Division of application No. 08/720,381, filed on Sep. 27, 1996, now Pat. No. 5,897,992.
(51) Int. Cl.⁷ .................. G01N 33/574; G01N 33/48; G01N 33/53; G01N 33/567; C12Q 1/00
(52) U.S. Cl. .................... 435/7.21; 435/4; 435/7.1; 435/7.23; 435/325; 435/352; 435/354; 435/29; 435/194; 435/357; 435/366; 435/367; 435/375; 514/12; 514/492; 424/277.1; 530/350; 436/63; 436/64; 436/86
(58) Field of Search .................. 435/4, 194, 7.1, 435/7.21, 7.23, 325, 352, 354, 29, 357, 366, 367, 375; 436/63, 64, 86; 514/12, 492; 424/277.1; 530/350

(56) References Cited

FOREIGN PATENT DOCUMENTS

| WO | WO 95/05738 | 3/1995 | .......... A01N/43/38 |
|---|---|---|---|
| WO | WO 96/20721 | 7/1996 | |
| WO | WO 96/26280 | 8/1996 | ........... C12N/15/57 |

OTHER PUBLICATIONS

American Type Culture Collection. Catalogue of Cell Lines and Hybridomas, 7th Edition. p. 170, 1992.*

Goldstein, W., "Apoptosis, When Suicide is Good" *Harbor Transcript*, A Newsletter of Cold Spring Harbor Laboratory, 14(1):1, 4–6, (1996).

Liu, Xuesong, et al., "Induction of Apoptotic Program in Cell–Free Extracts: Requirements for dATP and Cytochrome c", *Cell*, 86:147–157, (1996).

Lazebnik, Y.A., et al., "Studies of the lamin proteinase reveal multiple parallel biochemical pathways during apoptotic execution", *Proc. Natl. Acad. Sci. USA*, 92:9042–9046, (1995).

Nicholson, D.W., et al., "Identification and inhibition of the ICE/CED–3 protease necessary for mammalian apoptosis", *Nature*, 376:37–43, (1995).

Lazebnik, Y.A., et al., "Nuclear Events of Apoptosis In Vitro in Cell–free Mitotic Extracts: A Model System for Analysis of the Active Phase of Apoptosis", *Jour. of Cell Biol.*, 123(1):7–22, (1993).

Newmeyer, D.D., et al., "Cell–Free Apoptosis in Xenopus Egg Extracts: Inhibition by Bcl–2 and Requirement for an Organelle Fraction Enriched in Mitochondria", *Cell*, 79:353–364, (1994).

Cosulich, S.C., et al., "Bcl–2 regulates activation of apoptotic proteases in a cell–free system", *Current Biology*, 6(8):997–1005, (1996).

Lazebnik, Y.A., et al., "Cleavage of poly(ADP–ribose) polymerase by a proteinase with properties like ICE", *Nature*, 371:346–347, (1994).

Enari, M., et al., "Sequential activation of ICE–like and CPP32–like proteases during Fas–mediated apoptosis", *Nature*, 380:723–726, (1996).

Martin, S.J., et al., "Cell–free reconstitution of Fas–, UV radiation– and ceramide–induced apoptosis", *The EMBO Jour.*, 14(21):5191–5200, (1995).

Fisher, D.E., "Apoptosis in Cancer Therapy: Crossing the Threshold", *Cell*, 78:539–542 (1994).

Lowe, S.W., et al., "p53–Dependent Apoptosis Modulates the Cytotoxicity of Anticancer Agents", *Cell*, 74:957–967, (1993).

(List continued on next page.)

*Primary Examiner*—Alana M. Harris
(74) *Attorney, Agent, or Firm*—Hamilton, Brook, Smith & Reynolds, P.C.

(57) ABSTRACT

The present invention relates to a method of identifying a compound (agent) which modulates apoptosis in transformed cells. In one embodiment, the invention is a method of identifying a compound which selectively activates apoptosis in transformed cells. In an alternative embodiment, the present invention can be used as a method of identifying a compound which inhibits apoptosis in cells. The invention also relates to a method of selectively killing transformed cells, wherein the transformed cell is contacted with a compound which selectively activates apoptosis in transformed cells, as described herein. The invention also relates to methods of treating diseases associated with defective apoptotic machinery (e.g., cancer, neurodegenerative disease). The methods of the present invention are useful for defining the biochemical mechanisms of apoptosis. In addition, the invention provides an assay to identify compounds which modulate (inhibit, activate) apoptosis, supplying new drugs which target defective apoptotic machinery associated with disease (e.g., cancer, neurodegenerative diseases such as Huntington's Disease and Alzheimers Disease).

20 Claims, 6 Drawing Sheets

OTHER PUBLICATIONS

Rao, L. et al., "The adenovirus E1A proteins induce apoptosis, which in inhibited by the E1B 19kDa and Bcl–2 proteins", *Proc. Natl. Acad. Sci. USA, 89*:7742–7746, (1992).

Lowe, S.W., and Ruley, H.E., "Stabilization of the p53 tumor suppressor is induced by adenovirus 5 E1A and accompanies apoptosis", *Genes & Development, 7*:535–545, (1993).

Lowe, S.W., et al., "Abrogation of oncogene–associated apoptosis allows transformation of p53–deficient cells", *Proc. Natl. Acad. Sci. USA, 91*:2026–2030 (1994).

Lazebnik, Y.A., et al., "Characterization of the execution phase of apoptosis in vitro using extracts from condemned–phase cells", *Journal of Cell Science, Supplement, 19*:41–49, (1995).

White, E., "Life, death, and the pursuit of apoptosis", *Gene & Development, 10*:1–15, (1996).

Chinnaiyan, A.M., et al., "Molecular Ordering of the Cell Death Pathway", *J. Biol. Chem., 271*(9):4573–4576, (1996).

Enari, M. et al., "Apoptosis by a cytosolic extract from Fas–activated cells" *The EMBO J.., 14*(21):5201–5208 (1995).

Martin, S. J., et al., "Protease Activation during Apoptosis: Death by a Thousand Cuts?", *Cell, 82*:349–352 (1995).

Boulakia, C.A. et al., "Bcl–2 and adenovirus E1B 19 kDA protein prevent E1A–induced processing of CPP32 and cleavage of poly(ADP–ribose)polymerase", *Oncogene, 12*:529–535 (1996).

Fernandes–Alnemri, T., et al., "Mch3, a Novel Human Apoptotic Cysteine Protease Highly Related to CPP32[1]", *Cancer Research, 55*:6045–6052 (1995).

Kumar, S., et al., "ICE–like proteases in apoptosis", *Trends in Biochem. Sci., 20*:198–202 (1995).

Nunez, G., et al., "The Bcl–2 family of proteins: regulators of cell death and survival", *Trends in Cell Biol., 4*:399–403 (1994).

Sabbatini, P., et al., "Interleukin 1β Converting Enzyme–like Proteases Are Essential for p53–mediated Transcriptionally Dependent Apoptosis", *Cell Growth and Differen., 8*:643–653 (1997).

McCurrach, M.E., et al., "*bax*–deficiency promotes drug resistance and oncogenic transformation by attenuating p53–dependent apoptosis", *Proc. Natl. Acad. Sci. USA, 94*:2345–2349 (1997).

Fearnhead, H.O., et al., "Oncogene–dependent apoptosis in extracts from drug–resistant cells", *Genes and Develop., 11*:1266–1267 (1997).

Watabe, M., et al., "The Cooperative Interaction of Two Different Signaling Pathways in Response to Bufalin Induces Apoptosis in Human Leukemia U937 Cells", *J. Biol. Chem., 271*(24):14067–14073 (1996).

Faleiro, L., et al., "Multiple species of CPP32 and Mch2 for the major active caspases present in apoptotic cells", EMBO J., 16(9):2271–2281 (1997).

* cited by examiner

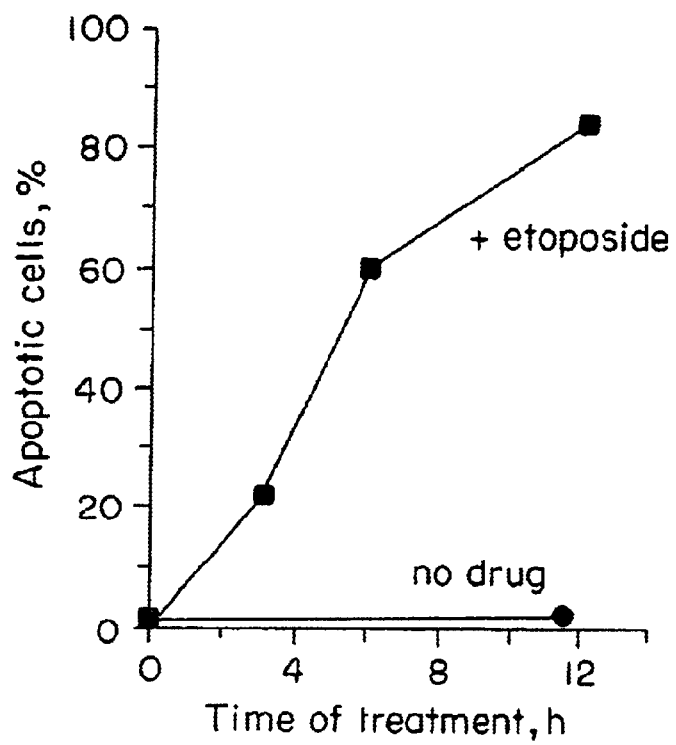
FIG. IA
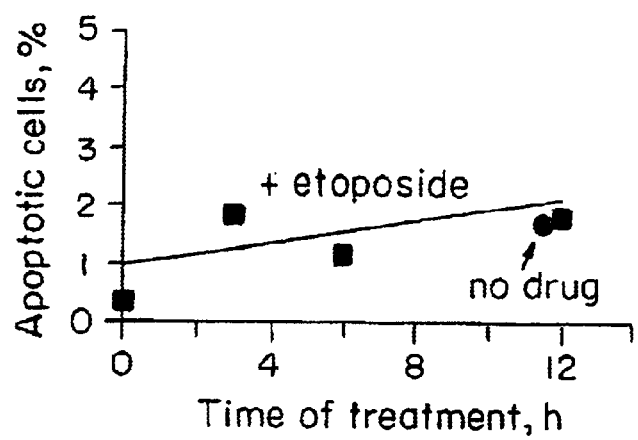
FIG. IB

CELL-FREE ASSAY USING ONCOGENE-INDUCED APOPTOSIS TO IDENTIFY INHIBITORS OF APOPTOSIS IN DRUG-RESISTANT CELLS

RELATED APPLICATION(S)

This is a Divisional Application of U.S. application Ser. No. 08/720,381 entitled "Cell-Free Assay Using Oncogene-Induced Apoptosis in Drug-Resistant Cells" by Howard O. Fearnhead et al. filed on Sep. 27, 1996 now U.S. Pat. No. 5,897,992. The entire teachings of U.S. application Ser. No. 08/720,381 is incorporated herein by reference.

BACKGROUND OF THE INVENTION

Apoptosis is a form of cell death that is carried out by a specialized intrinsic machinery. Although the knowledge about the biochemical mechanisms of apoptosis is fragmentary, it appears that signalling pathways that regulate apoptosis converge on a conserved machinery that disassembles a cell. An essential part of this machinery is a family of proteases related to interleukin-1B-converting enzyme (ICE) (Lazebnik, Y. A., et al., *Proc. Natl. Acad. Sci. USA*, 92:9042–9046 (1995); (Lazebnik, Y. A., et al., *Nature*, 371:346–347 (1994); Nicholson, D. W., et al., *Nature*, 376:37–43 (1995); Yuan, J., et al., *Cell*, 641–652:641–652 (1993)). ICE-like proteases (ILPs) are expressed as inactive pro-enzymes that have to be activated to cleave their substrates and to contribute to apoptosis (Horvitz, H. R., et al., *Cold Spring Harb. Symp. Quant. Biol.*, 59:377–385 (1994); Oltvai, Z. N. and Korsmeyer, S. J., *Cell*, 79:189–192 (1994)).

Cancer chemotherapy kills cells by induction of apoptosis (Lowe, S. W., et al., *Cell*, 74:957–967 (1993); Fisher, D. E., *Cell*, 78:539–542 (1994)). Defects of apoptosis common in cancer cells contribute to tumor regression and appear to be responsible for the failure of current cancer chemotherapy. Alternatively excess apoptosis can lead to neurodegenerative diseases (e.g., Huntington's Disease, Alzheimers Disease).

Therefore, more effective chemotherapeutic agents are needed.

SUMMARY OF THE INVENTION

The present invention relates to a method of identifying a compound (agent) which modulates apoptosis in transformed cells. In one embodiment, the invention is a method of identifying a compound which selectively activates apoptosis in transformed cells. In an alternative embodiment, the present invention can be used as a method of identifying a compound which inhibits apoptosis in cells.

The present method is carried out in a cell-free system in which the combination or reagents is determined by whether the assay is used to identify a compound which selectively activates apoptosis in transformed cells or a compound which inhibits apoptosis in cells.

In the embodiment in which a compound which selectively activates apoptosis in transformed cells is to be identified, the following reagents are combined to produce a test sample: the compound to be assessed; apoptotic machinery and a signal which activates the apoptotic machinery (e.g., obtained from cellular extracts of transformed cells); and an inhibitor of apoptosis. The combination is maintained under conditions appropriate for activation of apoptosis; activation of apoptosis is detected in the presence of the compound to be assessed by detecting or assessing an event indicative of recoupling of the apoptotic machinery. Recoupling of the apoptotic machinery indicates that the compound to be assessed selectively activates apoptosis in transformed cells.

In the embodiment in which an inhibitor of apoptosis is to be identified, the following reagents are combined: a compound to be assessed and apoptotic machinery and a signal which activates, or is capable of activating, the apoptotic machinery. The combination is maintained under conditions appropriate for activation of apoptosis; inhibition of apoptosis is detected in the presence of the compound to be assessed by detecting uncoupling of the apoptotic machinery. Uncoupling of the apoptotic machinery indicates that the compound to be assessed inhibits apoptosis in cells.

The invention also relates to a method of selectively killing transformed cells, wherein the transformed cell is contacted with a compound which selectively activates apoptosis in transformed cells, as described herein. The invention also relates to methods of treating diseases associated with defective apoptotic machinery (e.g., cancer, neurodegenerative disease). In one embodiment, the invention relates to a method of treating cancer in an individual, wherein an effective amount of a compound which selectively activates apoptosis in transformed cells is administered to the individual. In another embodiment, the invention relates to a method of treating a neurodegenerative disease in an individual, wherein an effective amount of a compound which modulates apoptosis, as identified herein, is administered to an individual.

The methods of the present invention are useful for defining the biochemical mechanisms of apoptosis. In addition, the invention provides an assay to identify compounds which modulate (inhibit, activate) apoptosis, supplying new drugs which target defective apoptotic machinery associated with disease (e.g., cancer, neurodegenerative diseases such as Huntington's Disease and Alzheimers Disease).

The invention further provides an alternative to current chemotherapy techniques. Current chemotherapy results in increasing the apoptotic signal by inflicting cellular damage in cancer cells and normal cells. However, this approach fails when the signal required to exceed the threshold in drug-resistant cells is sufficient to overcome the threshold in untransformed cells. As described herein, transformed cells harbor a signal which is capable of activating the apoptotic machinery in transformed cells. This signal, which is absent in untransformed cells, is uncoupled from the apoptotic machinery in drug-resistant cells. Thus, in contrast to current chemotherapy, compounds identified as described herein, which recouple the signal to the apoptotic machinery, will selectively kill these cells, and result in a more effective treatment for cancer.

BRIEF DESCRIPTION OF THE DRAWINGS

FIG. 1A is a graph of time of treatment versus % apoptotic cells illustrating induction of apoptotic morphology in intact Jurkat cells by etoposide.

FIG. 1B is a graph of time of treatment versus % apoptotic cells illustrating induction of apoptotic morphology in intact 293 cells by etoposide.

DETAILED DESCRIPTION OF THE INVENTION

Figure 2:
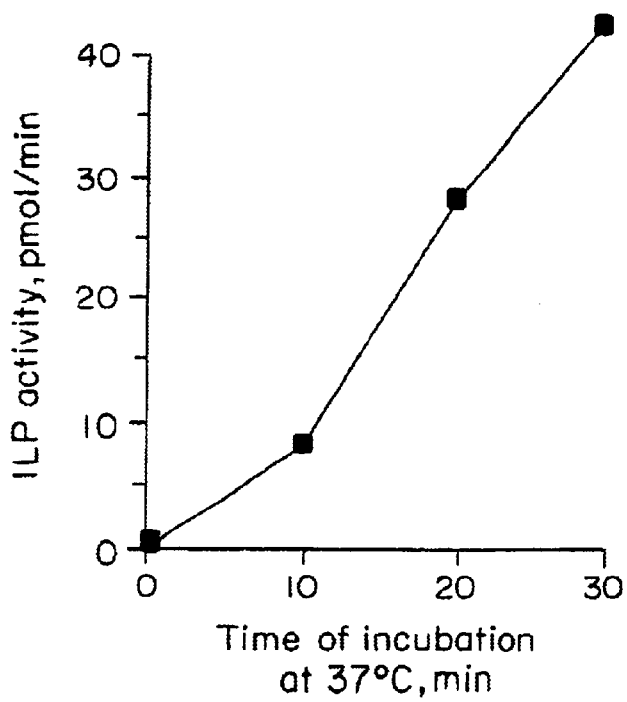
FIG. 2 is a graph of incubation time at 37° C. versus ILP activity, illustrating that ILPs are activated in extracts from 293 cells.

Described herein is a system that permits modulation of the apoptotic or suicide machinery in vitro. A system that reproduces inhibition of this activation by an agent (e.g., protein) that confers drug-resistance to cancer cells has also been developed.

The present invention is a method of identifying a compound which modulates (activates or inhibits) apoptosis. The method is carried out in a cell-free system in which the combination of reagents is determined by whether the assay is used to identify an activator or inhibitor of apoptosis.

In one embodiment, the present invention relates to a method of identifying a compound which selectively activates (induces or enhances) apoptosis in transformed cells. In this embodiment, the following reagents are combined to produce a test sample: the compound to be assessed; apoptotic machinery and a signal which activates the apoptotic machinery (e.g., obtained from cellular extracts of transformed cells); and an inhibitor of apoptosis. The combination is maintained under conditions appropriate for activation of apoptosis; activation of apoptosis is detected in the presence of the compound to be assessed by detecting or assessing an event indicative of recoupling of the apoptotic machinery. Recoupling of the apoptotic machinery indicates that the compound to be assessed selectively activates apoptosis in transformed cells.

In another embodiment, the present invention relates to a method of identifying a compound which inhibits apoptosis in cells. In this embodiment, the following reagents are combined to produce a test sample: a compound to be assessed; and apoptotic machinery and a signal capable of activating the apoptotic machinery. The combination is maintained under conditions appropriate for activation of apoptosis; inhibition of apoptosis is detected in the presence of the compound to be assessed by detecting uncoupling of the apoptotic machinery. Uncoupling of the apoptotic machinery indicates that the compound to be assessed inhibits apoptosis in cells.

Any suitable inhibitor of apoptosis can be used in the method of the present invention. For example, as described in the examples, bcl-2 can be used as an inhibitor of apoptosis in the methods of the present invention. Additional inhibitors of apoptosis which can be used include, but are not limited to, vanadate, E1B-19K, mutated p53, phosphotyrosine; $ZN^{2+}$, Crm A, and p35 (Beidler, D. R., et al., *J Biol. Chem.* 270:16526–16528 (1995); Lazebnik, Y. A., et al., *J Cell. Biol.*, 123:7–22 (1993); Martin, S. J., et al., *EMBO J.*, 14:5191–5200 (1995); Newmeyer, D. D., *Cell*, 79:353–364 (1994)).

As described herein, the cell-free assay utilizes apoptotic machinery and a signal capable of activating the apoptotic machinery. The apoptotic machinery, as defined herein, includes all of the signalling pathways that regulate apoptosis or portions of the apoptotic machinery which reproduce the suicide machinery of apoptosis when activated by the signal. For example, interleukin-1B-converting enzyme (ICE)-like proteases (ILPs) can be used with the signal capable of activating the ILPs in the methods described herein to identify compounds which activate or inhibit apoptosis. Other examples of a portion of the apoptotic machinery which can be used with a signal capable of activating the machinery for use in the present invention include the endonuclease activity of apoptosis. Identification of other portions of the apoptotic machinery which are activated by a signal capable of activating the machinery for use in the methods of the present invention can be determined using methods described herein and methods known in the art.

The apoptotic machinery and signal capable of activating the machinery can be obtained from any suitable source. For example, as demonstrated herein, cellular extracts of transformed cells can be used as a source for all or a portion of the apoptotic machinery and signal which activates the machinery. Examples of cellular extracts from transformed cells (preferably mammalian) which can be used to obtained the apoptotic machinery and signal include 293 cells, HeLa cells, transformed fibroblasts (e.g., mouse embryo fibroblasts (MEFS), human fibroblasts). In addition, extracts from other cells transformed with pro-apoptotic oncogenes (e.g., E1A, E7, c-myc, c-myb, cdc-25, E25, E2A-PBX1, ras; see (Bissonnette, R. P., et al., *Nature*, 359:552–556 (1992); (Fanidi, A., et al., *Nature*, 359:554–556 (1992); (Galaktionov, K., et al., *Nature*, 382:511–517 (1996); (Dedera, D. A., *Cell*, 74:833–843 (1993)) can be used in the methods of the present invention. Alternatively, all or a portion of the apoptotic machinery and the signal which activates the machinery can be chemically synthesized or obtained using recombinant techniques.

In the methods of identifying an activator or inhibitor of apoptosis described herein, the resulting combination is maintained under appropriate conditions (e.g., temperature, pH, sufficient time) for activation or inhibition of apoptosis. The present method can be carried out at a temperature from about 25° C. to about 40° C., preferably between about 30° C. to about 35° C., and even more preferably at 30° C. or 37° C. In addition, the treated sample can be incubated from about 10 minutes to about 120 minutes, preferably between 30 minutes to about 120 minutes, and more preferably for 30 minutes or 60 minutes. The method can be carried out as a series of steps or as a single (one-step) method. In the methods of the present invention, the following reagents must be present: a compound to be assessed, apoptotic machinery and a signal capable of activating the apoptotic machinery. Additionally, in the method in which a compound which selectively activates apoptosis in transformed cells is to be identified, an inhibitor of apoptosis must be present.

In addition, a control sample can be used in the methods of the present invention. For example, a control sample can be produced in which the same reagents are combined and processed in the same manner in the absence of the compound being assessed. Other suitable controls for use with the methods of the present invention can be determined using routine experimentation.

Various methods can be used to detect activation or inhibition of apoptosis in the presence of the compound being assessed. For example, the methods of the present invention can further comprise the step of adding cell nuclei wherein the morphological manifestations of apoptosis (e.g., nuclear chromatin condensation, blebbing of the nuclear, fragmentation of residual nuclear structures into discrete membrane-bounded apoptotic bodies, nuclei shrinkage; See Lazebnik, Y. A., et al., *J. Cell Biol.*, 123:7 (1993)) can be visualized in the presence of the compound to be assessed, using, for example, fluorescence microscopy. Cell nuclei for use in the present invention can be obtained from any suitable source using routine methods. For example, cell nuclei can be obtained from 293 cells, HeLa cells, fibroblasts (e.g., MEFs, human fibroblasts), and Jurkat cells. Alternatively, ILP activation, a biochemical hallmark of apoptosis, can be detected using, for example, an ILP affinity probe (e.g., biotin-YVAD-acyloxymethylketone). ILP activation can also be measured on a synthetic fluorogenic substrate (e.g., DEVD-AFC, DEVD-AMC), on a natural substrate (e.g., PARP), or by processing of cpp32, an ILP implicated in apoptosis. Other suitable methods of detection can be determined by those of skill in the art.

The present invention can also be used to selectively killing transformed cells wherein the transformed cell is contacted with a compound which selectively activates apoptosis in transformed cells, as described herein.

The invention can further be used to treat cancer wherein an effective amount of a compound which selectively activates apoptosis in transformed cells is administered to the individual. As described herein, "an effective amount" of a compound is an amount such that when administered, it results in prevention, amelioration or elimination of the cancer in the individual, compared to an individual who does not receive the compound. In addition, the amount of the compound will vary depending on the size, age, body weight, general health, sex, and diet of the host, and the time of administration, duration or particular qualities of the cancer. Adjustment and manipulation of established dose ranges are well within the ability of those of skill in the art.

The compound can be administered to the individual in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compound can be administered together with other components or biologically active agents, such as pharmaceutically acceptable surfactants (e.g., glycerides), excipients (e.g., lactose), carriers, diluents and vehicles.

Thus in the method of the present invention a mammalian cell-free apoptosis system that does not require an exogenous agent to activate the apoptotic machinery is used. The present invention is based on the discovery that certain cells (e.g., E1A transformed cells, E7 transformed cells) contain an endogenous signal which is sufficient to induce apoptosis. The signal is uncoupled from the apoptotic machinery (latent) in drug-resistant cells (e.g., transformed cells resistant to chemotherapy). Thus, agents that re-couple the signal to the machinery selectively kill these cells.

The present invention is illustrated by the following examples, which are not intended to be limiting in any way.

EXAMPLES

Example 1

Oncogene-induced Apoptosis in Extracts From Drug-resistant Cells

Experimental Procedures

Cell Culture 293 cells were maintained in suspension at 37° C. in Joklik modified minimum essential medium supplemented with 5% calf serum. Jurkat cells were maintained in suspension at 37° C. in RPMI-1640 supplemented with 10% fetal bovine serum.

Cell Transformation.

Transformed and untransformed MEFs were maintained at 37° C. and 7.5% $CO_2$ in DMEM supplemented with 10% calf serum.

Extract Preparation From 293 Cells and MEFs.

Extracts were prepared essentially as described (Lazebnik, Y. A., et al., *J. Cell. Biol.*, 123:7–22 (1993)). 293 cells (5–7×10$^5$ cells/ml)were washed and gently resuspended in 10×pellet volumes of extract preparation buffer (50 mM PIPES pH 7.0, 50 mM KCl, 5 mM EGTA, 2 mM $MgCl_2$, 1 mM DTT) plus 0.1 mM PMSF, 10 µg/ml cytochalasin B and 2 µg/ml each of chymostatin, pepstatin, leupeptin and antipain. Cells were immediately centrifuged (200 g, 5 minutes) and lysed by three cycles of freeze/thawing with liquid nitrogen. The lysate was centrifuged at 100,000 g for two hours, giving a cell extract. One liter of 293 cells yielded about 0.8 ml of extract with a protein concentration in the range 14–16 mg/ml. Extracts from MEFs were produced by the same protocol. MEFs were grown to confluence, detached from the plates with trypsin and washed with medium containing 50% fetal bovine serum to inactivate trypsin. Twenty 10 cm plates of MEFs yielded about 0.2 ml of extract with a protein concentration in the range 11–13 mg/ml. Extracts were aliquoted and stored at −70° C. for up to two months.

Preparation of HeLa Nuclei.

HeLa nuclei were prepared essentially as described (Lazebnik, Y. A., et al., *J. Cell. Biol.*, 123:7–22 (1993)). HeLa cells (5×10$^5$/ml) were washed and resuspended in nuclei buffer (10 mM PIPES, pH 7.4, 10 mM KCl, 1.5 mM $MgCl_2$, 1 mM DTT, 1 mg/ml cytochalasin B and protease inhibitors as for buffer A). Cells were allowed to swell on ice for 20 minutes and then gently lysed with a Dounce homogenizer. The nuclei suspension was layered over 30% sucrose and centrifuged (800 g, 5 minutes). The pelleted nuclei were washed once in nuclei buffer and stored at −70° C. in nuclei storage buffer (10 mM PIPES, pH 7.4, 80 mM KCl, 20 mM NaCl, 250 mM sucrose, 5 mM EGTA, 1 mM DTT, 0.5 mM spermidine, 0.2 mM spermine, protease inhibitors and 50% glycerol) at 1×10$^8$ nuclei/mi. Immediately before use nuclei were washed in buffer mitotic dilution buffer (MDB) (10 mM HEPES, pH 7.0, 50 mM NaCl, 2 mM $MgCl_2$, 5 mM EGTA, 1 mM DTT).

Expression and Purification of Bcl-2.

Before being added to extracts bcl-2 (0.4 mg/ml) was dialyzed against extract preparation buffer.

Microscopy.

Intact cells or isolated nuclei were fixed with 4% paraformaldehyde, stained with DAPI (1 µg/ml) and examined by fluorescence microscopy. The percentage of cells showing apoptotic nuclear morphology was determined. Images were acquired using a PHOTOMETRICS PXL CCD camera (Photometrics Ltd) contold by ONCOR Image software (Oncor Inc.). Figures were prepared using ADOBE PHOTOSHOP software.

Affinity Labeling of ILPs in Cells.

Biotinylated YVAD.AMK (10 mM stock solution in DMSO, Biosyn, Ireland) was aliquoted and stored at −70° C. Aliquots were diluted to 20 μM with MDB immediately before use.

Cells (2×10$^6$) were centrifuged (200 g, 5 minutes) and resuspended in 10 μM MDB containing 10 μM biotinylated YVAD.AMK (plus protease inhibitors and 10 mg/ml cytochalasin B) and lysed by freeze/thawing for three cycles. The lysate was centrifuged (16,000 g, 20 minutes, 4° C.) and the supernatant incubated at 37° C. for 4 minutes to label active ILPs. The protein concentration was determined (Bradford assay), an equal volume of 2×SDS sample buffer added and the sample boiled for 5 minutes.

Affinity Labeling of ILPs in Extracts.

Extracts were mixed with an equal volume of MDB containing 20 μM biotinylated YVAD.AMK and incubated at 37° C. for 4 minutes to label active ILPs. Labeling was stopped by adding an equal volume of 2×SDS sample buffer and samples were subjected to 15% SDS-PAGE. Proteins were transferred to a PVDF IMMOBILON P$^{SQ}$ membrane (Millipore Corp.) and the membrane washed (methanol, 5 minutes) and dried (80° C., 15 minutes). The blot was incubated with avidin (1 μg/ml) followed by Biotin-horse radish peroxidase (0.05 μg/ml), and labeled proteins detected by ECL (Amersham Inc.).

Immunoblotting for Cpp32.

Affinity blots were re-probed to detect cpp32. These membranes were soaked in methanol for 5 minutes to inactivate horseradish peroxidase, dried and re-probed with a monoclonal antibody to cpp32 (Transduction Laboratories) followed by incubation with a secondary antibody conjugated to horseradish peroxidase. The antigen-antibody complex was detected by ECL (Amersham Inc).

Immunoblotting for E1B-19K.

Samples were subjected to 15% SDS-PAGE and transferred (transfer buffer-50 mM Tris, 39 mM Glycine, 0.37% SDS, 10% methanol) to a PVDF IMMOBILON P$^{SQ}$ membrane (Millipore Corp.). The membrane was probed with a primary polyclonal antibody to E1B-19K (a gift from Bruce Stillman) followed by a secondary antibody conjugated to horse radish peroxidase. The E1B-19K-antibody complex was detected by ECL (Amersham).

Fluorescent Assay for ILP Activity.

ILP activity was measured using a microtitre plate assay essentially as described by (Thomberry 1994). One μl of extract was added to 200 μl of assay buffer (50 mM PIPES/KOH pH 7.0, 0.1 mM EDTA, 1 mM DTT, 10% glycerol) containing 20 μM DEVD-AFC (Enzyme Systems Products). The release of free AFC was measured with a fluorescence plate reader, CYTOFLUOR (Perseptive Biosystems).

RESULTS 293 cells are Resistant to Chemotherapeutic Dugs.

Jurkat cells (1×10$^5$/ml) (FIG. 1A) or 293 cells (1×10$^5$/ml) (FIG. 1B) were incubated with or without etoposide (50 μM). Cells were fixed at the indicated times and stained with DAPI. The percentage of cells with apoptotic nuclear morphology was determined. Samples were also taken to assess ILP activation.

293 cells were derived from human embryonic kidney cells by oncogenic transformation with adenovirus 5 DNA and express adenovirus E1A and E1B oncoproteins. This cell line was chosen as a model of drug-resistance because 293 cells are highly resistant to apoptosis induced by chemotherapeutics. Treatment with the chemotherapeutic drug etoposide induced no morphological signs of apoptosis in 293 cells at the concentration of the drug sufficient to kill Jurkat cells, a drug-sensitive T-leukemia cell line (FIGS. 1A, 1B).

To avoid relying solely on the morphological manifestations of apoptosis, whether activation of ILPs, a biochemical hallmark of apoptosis, occurred in 293 cells treated with etoposide was also determined. Jurkat cells (2×10$^6$) or 293 cells (2×10$^6$) were incubated with biotin-YVAD-AMK, an affinity probe that labels active ILPs. Samples (10 μg) were subjected to 15% SDS-PAGE and transferred onto a PVDF membrane. The membrane was probed with avidin followed by biotin-horse radish peroxidase and labeled ILPs visualized by ECL. To visualize ILPs activated in the cells an ILP affinity probe was used. The ILP affinity probes were biotin-labeled peptide inhibitors that bind irreversibly to the catalytic center of active ILPs and do not bind to ILP precursors (Miller, S. J., et al., *EMBO J.*, 14:5191–5200 (1995)). To detect active ILPs in the cells, the cells were lysed in the presence of biotin-YVAD-acyloxymethylketone, an ILP affinity probe, and incubated for 4 minutes at 37° C. The sample was then subjected to SDS-PAGE and the proteins were transferred onto a membrane. The blot was probed with the avidin-biotin detection system and positions of labeled ILPs were visualized by enhanced chemiluminescence. No active ILPs were detected in 293 cells treated with etoposide, whereas multiple active ILPs were detected in Jurkat cells treated with the same drug. This result indicated that not only morphological manifestations of apoptosis are absent in 293 cells treated with a chemotherapeutic drug but also the biochemical machinery of apoptosis is inactive.

Extracts From a Cell Line Resistant to Apoptosis Have Apoptotic Activity in a Cell-free System.

Cell-free extracts derived from cells that undergo drug-induced apoptosis are able to induce nuclear apoptotic changes in a cell-free system whereas extracts from untreated cells fail to do so. However, the latent apoptotic machinery is present in extracts from untreated cells and can be activated by addition of exogenous ILPs (Lazebnik, Y. A., et al., *J. Cell Sci. Supplement* 19;41–49 (1995)), granzyme B, a serine protease that can activate ILPs (Martin, S. J., et al., *EMBO J.*, 15:2407–2416 (1996)), ceramide (Martin, S. J., et al., *EMBO J.*, 14:5191–5200 (1995)), or dATP (Liu, X., et al., *Cell*, 86:147–157 (1996)). Therefore, whether the apoptotic machinery in an extract from untreated 293 cells can be activated by these reagents was determined.

293 cell extracts (10 μl) were incubated with isolated HeLa nuclei (1×10$^5$) for 60 minutes at 37° C. either alone or with biotin-YVAD-AMK (100 μM), an inhibitor of ILPs. After incubation aliquots of the reaction were fixed, stained with DAPI and examined by fluorescence microscopy.

Unexpectedly, an extract from untreated 293 cells, without any added agent, induced apoptosis in vitro. Isolated HeLa nuclei added to the 293 extracts underwent morphological changes typical of apoptosis within one hour upon incubation at 37° C. Virtually all nuclei treated with the extract had characteristic apoptotic morphology as illustrated by chromatin condensation and by nuclei shrinkage. To determine whether ILP activity was required for these nuclear changes biotin YVAD-amk, an inhibitor of ILPs, was added to the 293 cell extracts. This inhibitor prevented the nuclear morphological changes of apoptosis, suggesting that apoptosis in the extract from 293 cells required ILP activity. Hence, the results indicated that the extract from 293 cells has a functional apoptotic machinery.

The latter observation raised the question of why an extract from cells that are normally resistant to apoptosis contains an active apoptotic machinery? It is unlikely that the apoptotic activity of the 293 extract is an artifact of extract preparation, because extracts prepared from other untreated cell lines using identical or very similar protocols contain inactive ILPs and do not induce apoptosis in vitro. One explanation is that the extract from 293 cells contain not only the apoptotic machinery, but also the signal capable of activating it. This predicts that ILPs are initially inactive in the extract from 293 cells, as in extracts from other cell lines, but can be activated during extract incubation in a cell-free system.

To determine whether this prediction is true, three different assays were used. First, ILP activity was measured on the synthetic fluorogenic substrate DEVD-AFC (FIG. 2). Extracts were incubated at 37° C. and at the indicated times two aliquots were taken. One was assayed for activity against DEVD-AFC, a substrate for ILPs (FIG. 2).

Second, active ILPs were visualized by affinity labeling. Another aliquot was incubated with biotin-YVAD-AMK (10 $\mu$M), to label active ILPs. Samples (10 $\mu$g) were subjected to 15% SDS-PAGE and transferred to a PVDF membrane and labeled ILPs visualized by ECL.

Third, processing of cpp32, an ILP implicated in apoptosis, was followed by immunoblotting. The affinity blot discussed above was stripped and re-probed using an anti-cpp32 antibody and the antigen/antibody complex detected by ECL.

The extract from 293 cells initially had no detectable ILP activity, however, incubation of the extract at 37° C. resulted in ILP activation. Incubation of the extract on ice for at least five hours showed no ILP activation. ILP activity on the fluorogenic substrate was initially undetectable but increased dramatically during incubation of extracts at 37° C. (FIG. 2). The rate of ILP activation varied about two fold between different extract preparations. Results provided by affinity labeling were consistent with the data obtained with the fluorogenic substrate. No active ILPs were revealed in the extract initially, but multiple species of ILPs sequentially appeared in the extract incubated at 37° C. Finally, probing of the affinity blot with an anti-cpp32 antibody demonstrated that cpp32 was initially present in the extract from 293 cells as a precursor but was processed during incubation of the extract at 37° C. Thus, ILPs were extracted from 293 cells as precursors and were activated during incubation at 37° C. This novel finding suggested that in addition to a latent apoptotic machinery, 293 cells also contain an endogenous signal required for ILP activation.

Activation of Apoptotic Machinery in Extracts From MEFs Transformed With E1A and E1B but not in Extracts From Parental Cells.

A unique aspect of 293 cells compared to the few other cell lines used in cell-free systems is that they express adenovirus oncogenes E1A and E1B. E1A promotes apoptosis and E1B inhibits apoptosis. It was hypothesized that the signal capable of activating the apoptotic machinery in extracts from 293 cells is generated by the expression of E1A. To test this hypothesis extracts from primary cells were compared with extracts from cells transformed with E1A, or E1A plus E1B. Primary mouse embryo fibroblasts (MEFs) were selected as a model system because they have been used extensively to study the functions of E1A and E1B in transformation and apoptosis (Lowe, S. W., et al., *Proc. Natl. Acad. Sci. USA*, 91:2026–2030 (1994)).

An extract from MEFs transformed with E1A was compared to an extract from untransformed cells for their ability to induce apoptosis in vitro and to activate endogenous ILPs. Extracts (10 $\mu$l) from untransformed, E1A transformed or E1A/E1B transformed MEFs were incubated at 37° C. for 10 minutes before HeLa nuclei (1×10$^5$) were added and incubation continued for 60 minutes. After incubation nuclei were fixed, stained with DAPI and examined by fluorescence microscopy. Extracts (10 $\mu$l) from untransformed, E1A transformed or E1A/E1B transformed MEFs were incubated for 70 minutes at either 4° C. or 37° C. Active ILPs were labeled with biotin-YVAD-AMK (10 $\mu$M). Samples were subjected to 15% SDS-PAGE, transferred to a PVDF membrane and labeled ILPs visualized by ECL.

The extract from untransformed MEFs or MEFs transformed with the vector alone did not induce apoptosis in vitro, it did not contain active ILPs, nor did ILPs become active after incubation of the extract at 37° C. In contrast, the extract from MEFs transformed with E IA did induce apoptosis in vitro, and ILPs in this extract were activated during incubation at 37° C. Thus, ILPs were activated only in the extract from the cells transformed with E1A, suggesting that expression of E1A generates a signal capable of activating the apoptotic machinery in vitro.

No active ILPs were detected in the extract from untransformed MEFs even when incubated at 37° C. This could be due to two possibilities: the absence of either the activating signals or the ILP precursors. To test this, advantage of the observation that ICE can process ILPs in vitro (Xue, D. and Horvitz, H. R., *Cold Spring Harbor, N.Y.*, pp. 4 (1995)) was taken. Extracts from untransformed MEFs (10 $\mu$l) were incubated for 15 minutes at 37° C. with or without 0.9 units of recombinant ICE. Extracts from E1A/E1B MEFs (10 $\mu$l) were incubated for 15 minutes without ICE. Active ILPs were labeled with biotin-YVAD-AMK (10 $\mu$M). Samples were treated as described previously.

Addition of recombinant ICE to extracts from untransformed MEFs did activate endogenous ILPs demonstrating that ILP precursors are indeed present in the extract from the untransformed MEFs. Therefore, the signal capable of activating the ILP precursors was absent in this extract.

Extracts from MEFs expressing E1A or E1A plus E1B were also compared. Interestingly, extracts from both cell types induced apoptosis in vitro. Moreover, ILPs were also activated in extracts from both cell types by incubation at 37° C. This suggested that expression of E1B in the cells did not irreversibly inhibit the pro-apoptotic signal generated by expression of E1A.

Thus, the results obtained with the MEF system are consistent with the hypothesis that expression of the E1A oncoprotein in transformed cells generates the signal capable of activating the apoptotic machinery in cell-free extracts. The data suggests that this signal persists in cells expressing E1B, however, it is not clear why this signal is active in the extracts but fails to induce apoptosis in whole cells.

Extracts From E1A/E1B Transformed Cells are Depleted of E1B-19K, an Inhibitor of Apoptosis.

Figure 3:
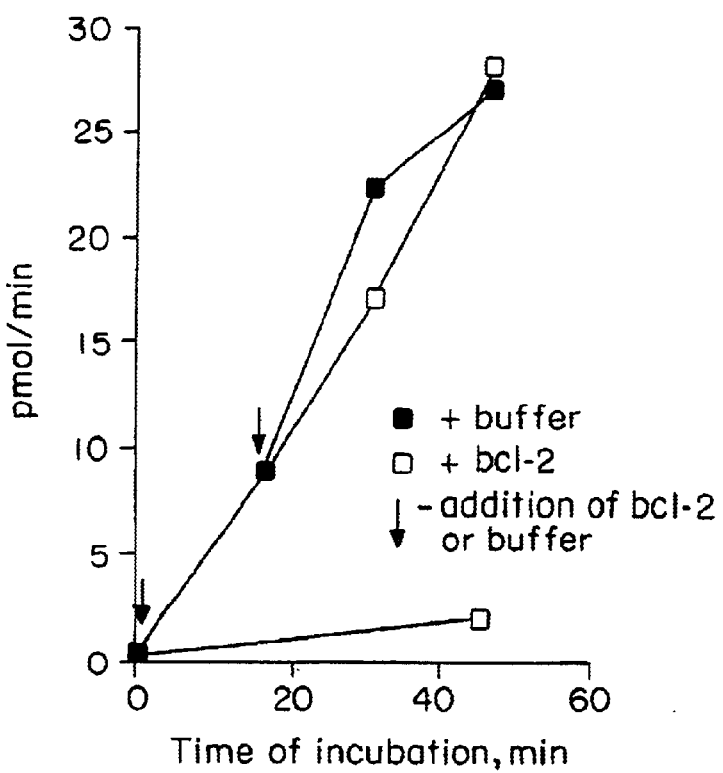
FIG. 3 is a graph of incubation time versus pmol (of AFC generated or cleaved DEVD-AFC) per minute, illustrating that bcl-2 inhibits ILP activation but not the ILP activity.

MEFs expressing E1A are highly prone to apoptosis (Lowe). In contrast, MEFs co-transformed with the anti-apoptotic oncogene E1B are highly resistant to apoptosis (Lowe, S. W. and Ruley, H. E., *Genes and Develop.*, 7:535–545 (1993); Rao, L., et al., *Proc. Natl. Acad. Sci. USA*, 89:7742–7746 (1992)). Nevertheless, the results demonstrate that extracts from both cell types activated endogenous ILPs and induced apoptosis in vitro (FIG. 3). This observation suggests that during extract preparation the anti-apoptotic effect of E1B is neutralized, allowing the proapoptotic activity generated by E1A to have a dominant effect.

The E1B oncogene encodes two proteins, E1B-55K and E1B-19K (White, E., *Curr. Top Microbiol. Immunol.*, 199:34–58 (1995); White, E., *Genes & Develop.*, 10:1–15 (1996)). Attention was focused on E1B-19K because this protein is a much more effective inhibitor of apoptosis than E1B-55K (Rao, L., et al., *Proc. Natl. Acad. Sci. USA*, 89:7742–7746 (1992)). Previous studies demonstrated that E1B-19K is highly hydrophobic and associates with cell membranes and intermediate filaments (White, E., et al., *Molecular and Cellular Biology*, 4:2865–2875 (1984)) suggesting the possibility that E1B-19K is not present in the extracts because of its poor solubility. Using an antibody to E1B-19K whether this protein is present in the extracts from 293 cells or from MEFs transformed with E1A and E1B was analyzed. During extract preparation from untransformed MEFs, E1A/E1B transformed MEFs or 293 cells an aliquot of total cell lysate (L) was taken before ultracentrifugation. After centrifugation (100,000 g) the pellet (P) was resuspended in a volume of extract buffer equal to that of extract (E) obtained. The protein concentration was determined by Bradford assay (Biorad). Samples subjected to 15% SDS-PAGE and E1B-19K detected by immunoblotting.

E1B-19K was not detectable in either extract, because it partitioned with the insoluble material. Bcl-2 has been shown to have similar distribution following cell fractionation, suggesting that other bcl-2-like proteins are also depleted from the extracts.

Thus activation of ILPs in the extracts may be explained by the absence of E1B-19K protein that was depleted during extract preparation.

In summary, the results obtained with the MEF system are consistent with the hypothesis that the pro-apoptotic signal generated by E1A oncoprotein is present in the cells but is uncoupled from the apoptotic machinery by products of E1B. In cell-free extracts the signal generated by E1A is revealed because the anti-apoptotic effect of E1B is abolished.

Bcl-2 Prevents ILP Activation and Apoptosis in Extracts From E1A/E1B Transformed Cells.

If E1B-19K inhibits ILP activation, then re-introduction of this protein to the extracts should prevent ILP activation and apoptosis in vitro. In agreement with previous reports (White, E., *Genes & Develop.*, 10:1–15 (1996)), recombinant E1B-19K was poorly soluble and native recombinant protein was not obtained. Recombinant bcl-2 was substituted for E1B-19K since bcl-2 can substitute for E1B-19K as an inhibitor of apoptosis in vivo (White, E., *Genes & Develop.*, 10:1–15 (1996)). In addition, both oncoproteins share structural similarity and interact with a common set of proteins (Boyd, J. M., et al., *Cell*, 79:341–351 (1994)). A soluble form of bcl-2 lacking the C-terminal hydrophobic region was used. bcl-2 lacking the transmembrane domain inhibits apoptosis in cells although to a lesser extent than native bcl-2 (Oltvai, Z. N. and Korsmeyer, S. J., 79, 79:189–1922 (1994); Oltvai, Z. N., etal., *Cell*, 74:609–619 (1993)).

Addition of bcl-2 prevented apoptosis in vitro in extracts from both 293 cells and MEFs transformed with E1A and E1B. Extracts from E1A/E1B transformed MEFs or 293 cells (10 $\mu$l) were incubated with bcl-2 (40 $\mu$g/ml) for 10 minutes at 37° C. prior to further incubation with HeLa nuclei (1×10$^5$) for 60 minutes. Nuclei were fixed, stained with DAPI and examined by fluorescence microscopy.

Prevention of apoptosis was achieved only if extracts were pre-incubated with bcl-2 before addition of nuclei. Extracts containing recombinant bcl-2 had no active ILPs, suggesting that bcl-2 inhibited either ILP activity or ILP activation. The same extracts were incubated alone, with buffer or with bcl-2 (40 $\mu$g/ml) for 70 minutes at 37° C. and active ILPs labeled with biotin YVAD.AMK (10 $\mu$M). Samples were subjected to 15% SDS-PAGE, transferred to a PVDF membrane and labeled ILPs visualized by ECL.

To determine whether bcl-2 blocks ILP activation or inhibits the enzymatic activity of ILPs, bcl-2 was added to extracts either before or after incubation at 37° C. and monitored ILP activity by a quantitative enzymatic assay. Bcl-2 (40 $\mu$g/ml) was added to 293 extract either before incubation at 37° C. or after 15 minutes of the incubation (additions indicated by arrows). ILP activity against DEVD-AFC was measured as described above (FIG. 3).

bcl-2 failed to block either ILP activity or the rate of ILP activation if added after 15 minutes of incubation, whereas ILP activity was blocked if bcl-2 was added at the beginning. This result indicates that bcl-2 inhibits the initiation of ILP activation, rather than ILP activity. Furthermore, bcl-2 fails to prevent the completion of ILP activation once some ILP activity is generated. This experiment provides the biochemical evidence that bcl-2 regulates activation of the apex of the ILP cascade, rather than each individual ILP molecule. Thus, these results are consistent with the hypothesis that E1B-19K protein uncouples the apoptotic machinery from the pro-apoptotic signal and the removal of E1B-19K, and perhaps other bcl-2 like proteins, allows ILP activation in the extracts.

DISCUSSION

The resistance of cancer cells to chemotherapy depends largely on alterations that inhibit apoptosis. Strategies that circumvent such alterations should be helpful in developing effective chemotherapeutics. To understand how alteration of apoptosis can cause drug-resistance, E1A/E1B transformed cells were used as a model. Using extracts from these cells a cell-free system that mimics apoptosis induced by expression of the E1A oncogene was developed. This system revealed that drug-resistant E1A/E1B transformed cells contain the pro-apoptotic signal generated by E1A. This signal is capable of activating the apoptotic machinery, however, in cells the machinery and the signal are uncoupled. Thus, drugs that will recouple the apoptotic machinery to the proapoptotic signal will be selective and efficient chemotherapeutics.

Oncogene-induced Apoptosis in a Cell-free System

Cell-free systems have been instrumental in determining molecular mechanisms of apoptosis by making the mechanisms accessible to biochemical approaches. However, a system that mimics activation of the mammalian apoptotic machinery by an endogenous signal has not been described. Several systems were reported where a latent apoptotic machinery present in cell extracts was activated by adding exogenous agents such as an active ILP (Enari, et al., *Nature*, 380:723–726 (1996)), serine protease granzyme B (Martin, S. J., et al., *The EMBO J.*, 14(21):5191–5200 (1995)), ceramide (Martin, S. J., et al., *The EMBO J.*, 14(21): 5191–5200 (1995)), or dATP (Liu, X., et al., *Cell*, 86:147–157 (July 1996); Boyd, J. M., et al., *Cell*, 79:341–351 (1994)). Although these systems provided insights into biochemistry of apoptosis, adding an exogenous trigger may activate the apoptotic machinery by a mechanism different from that in intact cells. The only extracts that acquire apoptotic activity due to an endogenous signal were derived from untreated Xenopus eggs (Newmeyer, D. D., et al., *Cell*, 79:353–364 (1994)) yet, the origin of this signal is not clear (Newmeyer, D. D., et al., *Cell*, 79:353–364 (1994); Cosulich, S. C., et al., *Current Biology*, 6(8):997–1005 (1996)).

Here the first mammalian cell-free system that required no exogenous agents to activate the apoptotic machinery has been developed. Apoptosis in this system mimics apoptosis in vivo according to several criteria. First, bcl-2, an inhibitor of apoptosis in vivo blocked apoptosis in vitro. Second, both morphological nuclear changes and their time course in the cell-free system were similar to those seen in cells undergoing apoptosis. In addition, the ILP activity required for apoptosis in vivo was also necessary for apoptosis in vitro. Furthermore, this activation was linked to expression of E1A in cells used as a source of the extracts.

E1A promotes apoptosis in cells (Nicholson, D. W., et al., Nature, 376:37–43 (1995)) but the molecular mechanisms of this process are obscure. The cell-free system described here mimics apoptosis induced by E1A, and makes this process accessible to biochemical analysis. In addition, identification of the E1A-generated signal should be facilitated by comparing apoptotic activity of extracts from cells with defined genetic differences, as described herein. For example the role of p53 can be addressed by comparing extracts from the cells expressing or lacking p53.

Activation of multiple ILPs in Fas-induced and, perhaps, other types of apoptosis, occurs sequentially, although which proteases are activated at each step is not clear (Chinnaiyan, A. M., et al., J. Biol. Chem., 271:4573–4576 (1996)). Delineation of this sequence has been difficult in part because cells undergo apoptosis asynchronously and a cell-free system that mimics this activation was not available. Cpp32, an ILP thought to play a major role in apoptosis (Nicholson, D. W., et al., Nature, 376:37–43 (1995)); was activated in extracts from 293 cells although affinity labeling suggested that other ILPs are involved. These putative ILPs were activated sequentially in distinct steps, suggesting that this system can be used to delineate ILPs involved in apoptosis.

An understanding of how activation of ILP is initiated is critical for understanding regulation of apoptosis. ILP activation results in rapid cleavage of cell proteins, destroying cell structures and activating other enzymes such as an endonucleases that contribute to cell destruction. The results show that bcl-2 cannot inhibit ILP activation once ILP activity appears in the extracts, suggesting that once ILP activation is initiated it proceeds to completion perhaps due to the ability of ILPs to activate each other in a proteolytic cascade. Thus, it appears that the activation of the ILP that initiates this cascade inevitably leads to death. An ILP activated early in 293 cell extracts was processed in the presence of ILP inhibitors, suggesting that it was activated not by other ILPs and is the ILP that lies at the apex of the cascade. Thus, this system can be used to identify the apical ILP and the processes involved in initiation of ILP activation.

Inhibition of ILP Activation by Bcl-2

Overexpression of bcl-2 in cells inhibits apoptosis and processing of ILPs although the mechanism of this inhibition is not clear (Chinnaiyan, A. M., et al., J. Biol. Chem., 271:4573–4576 (1996)). bcl-2 inhibition of apoptosis in a cell-free system was reproduced which allowed analysis of the effect of bcl-2 on activation of endogenous ILPs. Bcl-2 inhibited activation of ILPs but did not inhibit active ILPs.

Importantly, once ILP activity appeared, bcl-2 could no longer block ILP activation. An attractive model that explains these results is that bcl-2 prevents activation of the ILP that lies at the apex of the ILP cascade. Once this apical ILP is activated it becomes insensitive to bcl-2 and activates other ILPs required for apoptosis. Hence, bcl-2 may control activation of the cascade by a mechanism yet to be identified.

Models of how bcl-2 blocks apoptosis include interaction of bcl-2 with activators of apoptosis and regulation of membrane permeability of organelles such as ER and mitochondria. In the experiments described herein, bcl-2 inhibited ILP activation in extracts prepared by ultracentrifugation. These extracts may contain membrane fragments, but the presence of large organelles such as mitochondria is unlikely. Furthermore, bcl-2 lacking the transmembrane domain was used. These results strongly suggest that bcl-2 does not inhibit ILP activation by regulating membrane permeability.

It is reasonable to expect that the signal activating ILPs is a protein because dialysis of extracts did not prevent ILP activation. bcl-2 may interact with this protein thereby preventing ILP activation. Alternatively, bcl-2 may interact directly with the apical ILP or prevent recruitment of this ILP to an activating complex, such as described for Fas and TNF mediated apoptosis. Identification of proteins interacting with bcl-2 in the extracts will test this model and may explain how bcl-2 controls activation of the ILP that initiates irreversible events culminating in cell death.

Implications for Cancer Therapy

The data points to why E1A transformed cells are more sensitive or have a lower threshold (Fisher) to cytotoxic drugs than untransformed cells. It appears that expression of E1A generates a signal that is present in the cells and is capable of activating ILPs. However, inhibitors of apoptosis such as bcl-2 uncouple this signal from the apoptotic machinery. For example, if the signal is a protein, it may be bound by bcl-2 thereby preventing interaction with the apoptotic machinery. The level of the inhibitors establishes the threshold of the apoptotic signal required to activate ILPs and kill a cell. The presence of the E1A-generated signal lowers the amount of free inhibitor thus lowering the threshold for apoptosis. Therefore, E1A transformed cell are killed by a lower concentration of a cytotoxic drug than is required to kill untransformed cells. However, expression of E1B-19K, that mimics endogenous inhibitors of apoptosis, increases the threshold and results in drug resistance.

In tumors, this higher threshold may be brought about by overexpression of bcl-2 and other endogenous or viral bcl-2 like proteins. Thus, to activate ILPs and kill drug-resistant cells one needs to either increase the signal or inactivate the inhibitors that uncouple the signal from the apoptotic machinery. Current chemotherapy focuses on results in increasing the apoptotic signal by inflicting cellular damage. However, this approach fails when the signal required to exceed the threshold in drug-resistant cells is sufficient to overcome the threshold in untransformed cells. Moreover, such therapy selects for tumor cells with the higher threshold.

Data described here provides an alternative to current chemotherapy. Biochemical evidence that E1 A induced transformation generates a signal capable of activating the apoptotic machinery that persists even when the cells become drug resistant has been provided. This signal is absent in untransformed cells. The data suggest that decreasing the level of available anti-apoptotic proteins such as bcl-2 or E1B-19K will re-couple the E1A-generated signal to ILP activation. Since this signal is absent in untransformed cells, decreasing inhibitors of apoptosis should not lead to death. Studies published elsewhere support this prediction. Overexpression of bax, a protein that sequesters E1B-19K, induces apoptosis in E1A/E1B transformed cells (Han, J. H., et al., Gene Develop., 10:461–477 (1996)) but does not induce apoptosis in normal cells although makes them more sensitive to apoptosis-inducing agents. Agents that mimics the effect of bax and lower the concentration of free anti-apoptotic agents will be cytotoxic agents selective for E1A transformed cells even if they are resistant to current chemotherapeutics.

Although in this study E1A transformed cells were used as a model system, a growing number of oncogenes including myc (Evan, G., et al., *Cell*, 69:119,128 (1992)), myb (Sala, A., et aL, *Cancer Res.*, 56:1991–1996 (1996)), cdc 25 (Galaktionov, K., et al., *Nature*, 382:511–517 (1996)), and human papilloma virus E7 (Howes, K. A., et al., *Genes and Develop.*, 8:1300–1310 (1994)), also induce apoptosis. Extracts from untreated HeLa cells, a human cervical carcinoma cell line expressing E7, induce ILP activation. This suggests that oncogenes other than E1A may generate a pro-apoptotic signal that can selectively kill transformed cells.

Here biochemical evidence that transformed cells harbor a signal generated by the transforming oncogene and sufficient to induce apoptosis is provided. This signal is uncoupled from the apoptotic machinery in drug-resistant cells, which suggests that agents which re-couple the signal to the machinery will selectively kill these cells. The cell-free system described herein provides an assay to search for drugs that achieve this re-coupling of apoptosis.

Although it is not clear how activation of ILPs is controlled, it seems to depend on the balance between pro-apoptotic and anti-apoptotic regulators of apoptosis. A number of such regulators have been described. For example, the bcl-2 family of proteins contains both inhibitors of apoptosis such as bcl-2 itself and activators such as bax (Oltvai, et al., *Cell*, 74:609–619 (1993)). It is not clear how the members of bcl-2 family regulate apoptosis, although physical interactions between them are implicated in determining cell viability. Thus, apoptosis is controlled by a network of signalling pathways that either inhibit or promote activation of ILPs, an essential part of the apoptotic machinery (Lowe, S. W., et al., *Cell*, 74:957–967 (1993); Fisher, D. E., *Cell*, 78:539–542 (1994)).

A failure of such induction results in drug resistance. Alterations that prevent apoptosis are common in cancer cells. Two examples of such alterations are over-expression of bcl-2 and mutations of p53, a tumor suppressor that is critical for induction of apoptosis by a number of agents (Lowe, S. W., et al., *Cell*, 74:957–967 (1993)). Overexpression of bcl-2 that can occur as a result of a chromosomal translocation is common in follicular lymphomas (Tsujimoto, Y., et al., *Science*, 228:1440–1443 (1985)). Mutations of p53 have been detected in a majority of cancers (Levine, A. J., et al., *Nature*, 351:453–455 (1991))). Prevention of apoptosis is critical for carcinogenesis, as indicated by studies on oncogenic transformation by DNA tumor viruses. The adenovirus E1A oncogene, for instance, is sufficient to transform cells, but only if apoptosis is inhibited. However, transformed cells survive if a second adenovirus oncogene, E1B is also expressed. E1B encodes two anti-apoptotic oncoproteins, E1B-55K which interferes with p53 function and E1B-19K which is a structural and functional homologue of bcl-2. Similarly, papilloma virus contains E7, the oncogene required for transformation, and E6, the oncogene that inactivates apoptosis by targeting p53 for degradation. Hence, the failure to undergo apoptosis contributes to carcinogenesis.

Since chemotherapeutic drugs induce apoptosis, alterations in the regulatory pathways of apoptosis also promote drug resistance of cancer cells. Chemotherapeutic drugs do not kill cells directly at concentrations achieved in-vivo. Instead, they induce cell damage, such as DNA breaks, and this damage initiates a signal that activates the apoptotic machinery. Although different cytotoxic agents can induce different signals, these signals converge on the conserved pathway. As a result, alterations in this pathway result in drug resistance even prior to exposure to a drug. For example, drug resistance may be acquired by cells containing mutations in p53 or lacking this protein. Similarly, drug resistance results from overexpression of such inhibitors of apoptosis as bcl-2 or E1B-19K.

Example 2

Incubation of HeLa Cell Extracts at 37° C. Results in ILP Activation.

HeLa Extracts and ICE-like Protease Activation.

HeLa cells are a human cancer cell line derived from a cervical carcinoma.

These cells contain viral DNA from human papilloma virus that encodes early genes 6 (E6) and 7 (E7). E7 is like E1A, E7 induces apoptosis and thus efficient transformation requires a second oncogene. E6, which is in some ways analogous to E1B fulfills this role. It was determined whether the in vitro pro-apoptotic effects of E1A were limited only to E1A. It was predicted that because of the presence of E7, extracts from HeLa cells would also spontaneously activate ILPs. The results confirmed this prediction.

Extracts from 293, Jurkats, HeLa cells or E1A/E1B MEFs were incubated at 37° C. for 60 minutes. After this time active ILPs present in the extracts were labeled with an ILP affinity probe, Biotin-YVAD-AMK. Proteins of approximately 20 kDa were labeled in 293 and E1A/E1B extracts after incubation at 37° C. but no proteins were labeled in Jurkat extracts.

Figure 4:
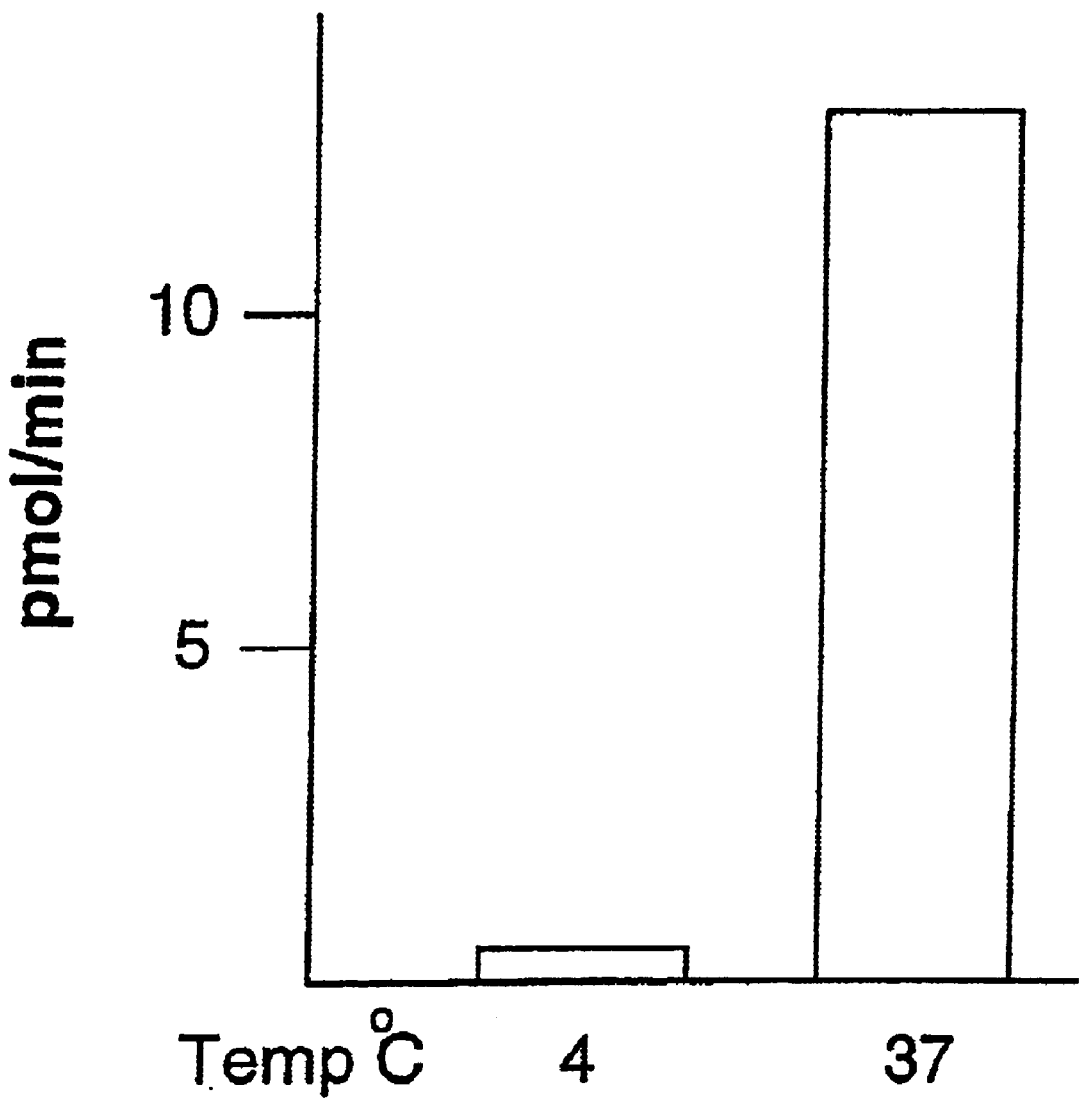
FIG. 4 is a graph of HeLa extracts versus pmol AFC generated per minute illustrating that ILPs are activated in extracts from HeLa cells.

HeLa cells ($1\times10^5$) were maintained in spinner culture at 37° C. Extracts were prepared exactly as for 293 cell extracts. HeLa cell extracts were incubated with an ATP generating system for 60 minutes either at 4° C. or at 37° C. In one experiment active ILPs were affinity labeled with biotin-YVAD-AMK as described in Example 1. In one experiment ILP activity was assayed using a fluorimetric protease assay as described in Example 1 (FIG. 4). The results indicate ILP activation in extracts from 293 cells and E1A/E1B MEFs and are in agreement with the previous observations. In addition proteins were also labeled in HeLa extracts following incubation at 37° C., indicative of ILP activation. To corroborate this observation, ILP activity in HeLa cell extracts was measured using a fluorimetric assay. This showed that while little or no ILP activity was detectable in HeLa extracts incubated at 4° C. for 60 minutes, after 60 minutes at 37° C. ILP activity appeared. Thus, like E1A/E1B MEF and 293 cell extracts, HeLa cell extracts contain an endogenous signal capable of activating ILPs.

Example 3

Vanadate Inhibits Activation of ILPs but not Activity of ILPs.

As described herein extracts from 293 cells contain inactive ILPs that are activated by shifting the extracts to 37° C. Therefore, this system can be used not only to study the biochemistry of induction of apoptosis by E1A but also to study activation of ILPs involved in apoptosis. This was confirmed by using the system to search for compounds that affect ILP activation. Such compounds can be used as tools to study ILP activation and supply leads about potential new drugs that target the apoptotic machinery.

As described below, the system described above can be used to screen for compounds that effect ILP activation.

Such compounds inhibit ILP activation but have no effect on ILPs after they have become active. To do this compounds were added to extracts before ILPs were activated or after activation had occurred and ILP activity determined by fluorimetric assay. Vanadate (0.1, 1 and 5 mM) was added to extracts from 293 cells and the extracts then shifted to 37° C. and incubated for 30 minutes. The rate of DEVD-AFC proteolysis was then determined. Vanadate inhibited cleavage of DEVD-AFC if added before shifting the extract to 37° C.

Figure 5A:
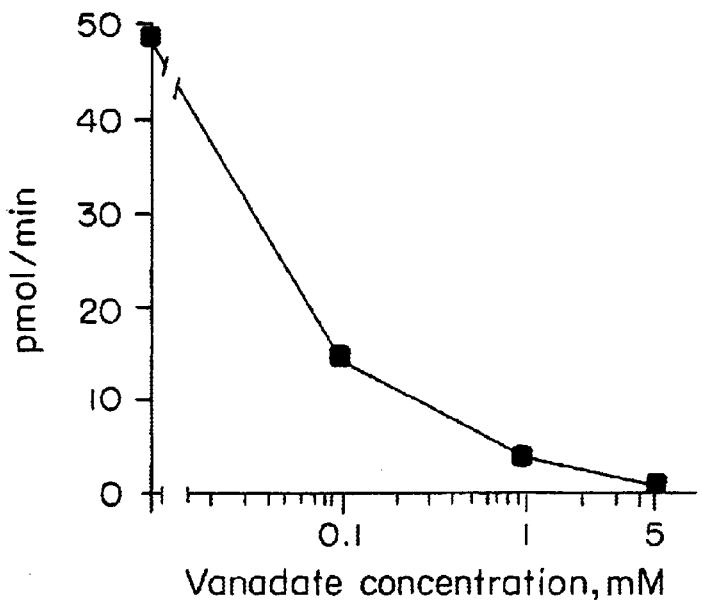
FIG. 5A is a graph of vanadate concentration versus pmol AFC generated per minute, illustrating sodium ortho vanadate blocks ILP activation but not ILP activity.

It was found that sodium ortho vanadate (vanadate) blocked ILP activation but not ILP activity. Vanadate prevented activation of ILPs in the cell free system (FIG. 5A). Addition of vanadate to extracts before shifting them to 37° C. decreased the rate of ILP activation. The concentration dependence of inhibition (FIG. 5A) varied between extracts but in all extracts 5 mM caused complete inhibition.

Figure 5B:
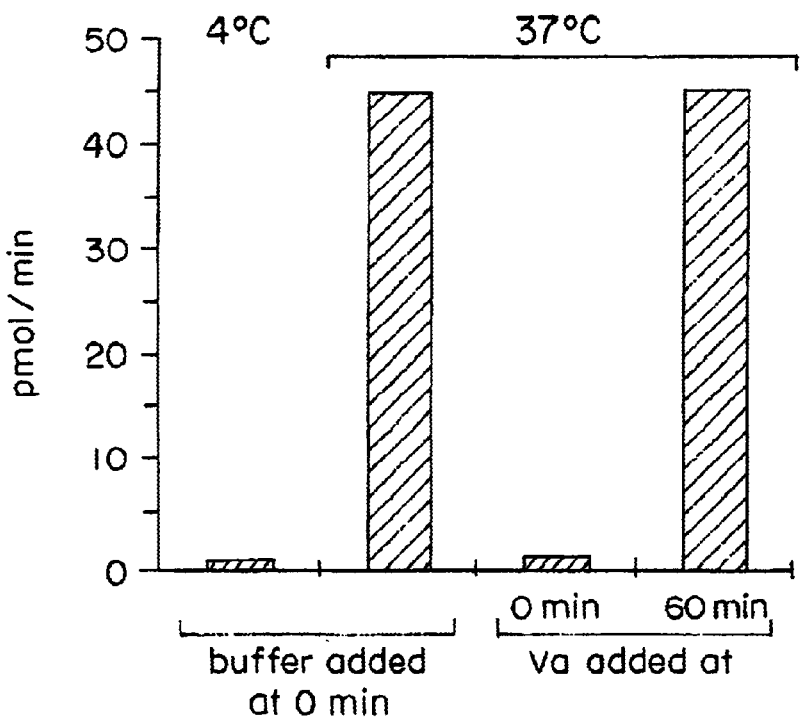
FIG. 5B is a histogram illustrating vanadate blocks ILP activation.

Vanadate did not block cleavage of DEVD-AFC if added to an extract after incubation for 60 minutes. Vanadate (5 mM) was added to extracts either before 60 minutes incubation at 37° C. or after 60 minutes incubation. The extracts were then incubated for a further 60 minutes and the rate of DEVD-AFC proteolysis determined. Adding vanadate after ILPs were already active had no effect on ILP activity (FIG. 5B).

Figure 6:
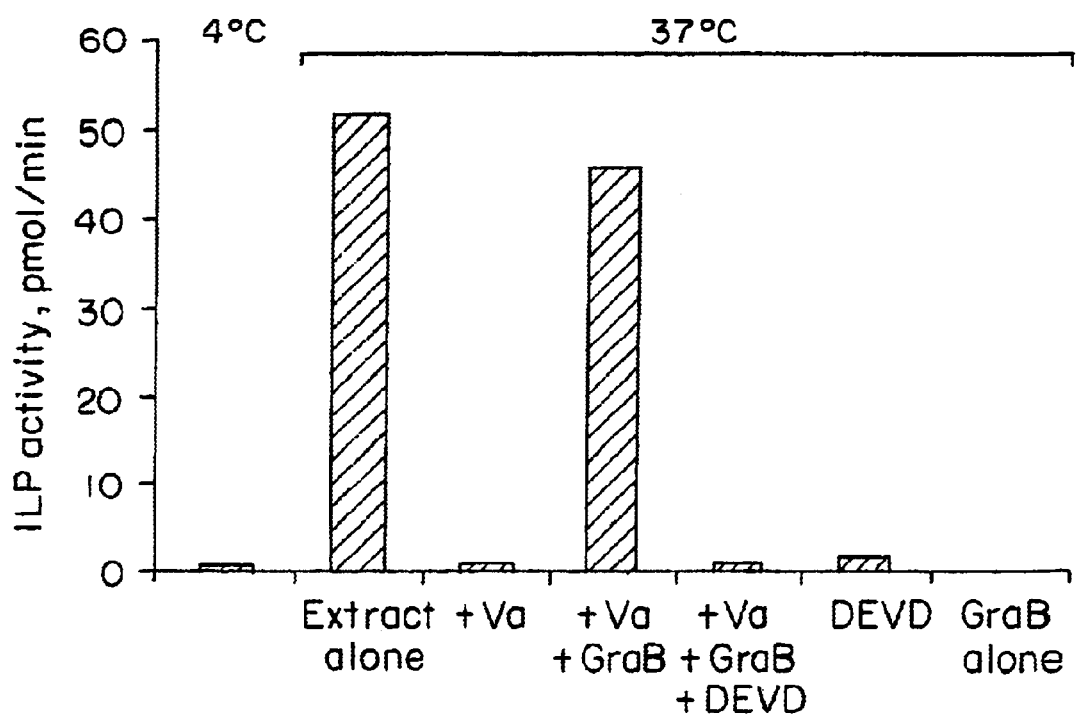
FIG. 6 is a histogram of treated extracts illustrating granzyme B activates ILPs in the presence of vanadate.

Granzyme B, a serine protease which activates ILPs directly, was used to confirm that vanadate blocked activation but not activity of ILPs. Granzyme B is a serine protease required for induction of apoptosis in target cells by cytotoxic T cells and natural killers. It is believed that Granzyme B does so by activating cpp32 and bypassing normal regulatory mechanisms that prevent ILP activation. Therefore whether Granzyme B bypassed vanadate inhibition of ILP activation was investigated. To do this Granzyme B was added to extracts treated with vanadate and determined both the rate of ILP activity (FIG. 6) and the ability of the extracts to induce apoptosis in vitro. Extracts from 293 cells were incubated for 60 minutes at 37° C. Where indicated vanadate (5 mM), Granzyme B (2 U/ul) or DEVD-CMK (10 μM) was added before the extract was shifted to 37° C. After 60 minutes the rate of DEVD-AFC proteolysis was determined. Data is representative of two experiments. In parallel, nuclei ($1 \times 10^7$/ml) were incubated at 37° C. for 60 minutes with extracts treated with vanadate (5 mM), Granzyme B (2 U/ul ) or DEVD-CMK (10 μM) where indicated. Nuclei were also incubated at 4° C. with extract or at 37° C. with Granzyme B but no extract.

Addition of Granzyme B completely overcame vanadate inhibition with respect to both ILP activity and in vitro apoptosis. Two additional criteria, affinity labeling and immuno-blotting confirmed that addition of Granzyme B to extracts treated with vanadate resulted in ILP activation and cpp32 processing. Thus, vanadate inhibited ILP activation but failed to inhibit ILP activity.

Interestingly, although an ILP inhibitor blocked in vitro apoptosis, it was noted that in the presence of both an ILP inhibitor and Granzyme B extracts still induced some morphological changes in isolated nuclei. These were reminiscent of early stages of apoptosis but were distinct from apoptotic nuclei. This suggests that the role of Granzyme B in apoptosis is not restricted to the activation of ILPs.

ILP Activity is not Sufficient for ILP Activation.

Figure 7:
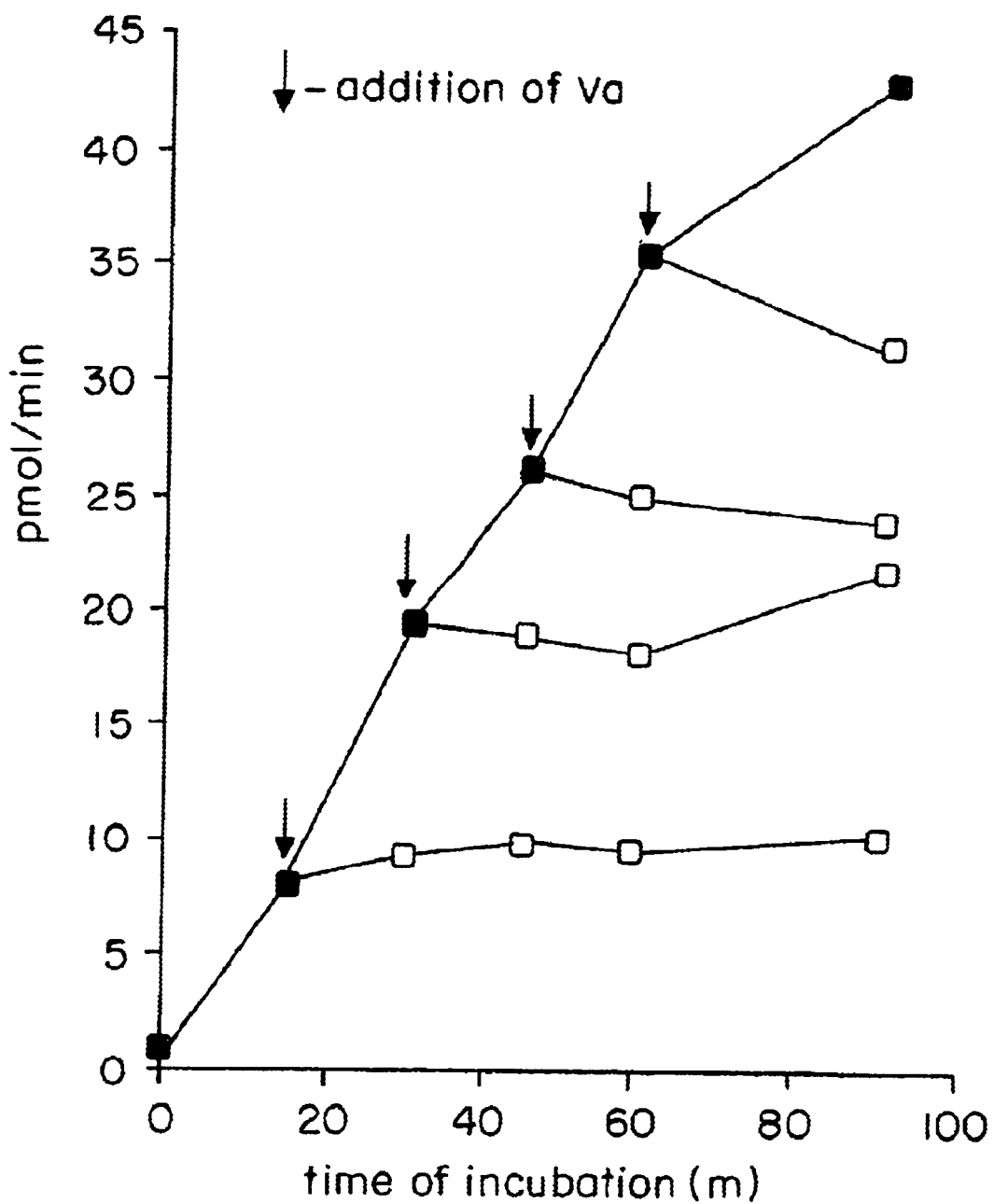
FIG. 7 is a graph of incubation time versus pmol AFC generated per minute illustrating ILP activity is not sufficient for ILP activation.

Having identified a compound that inhibited ILP activation but not ILP activity, the ILP activation during apoptosis was dissected. When the vanadate sensitive activity was necessary for ILP activation was determined. Vanadate was added to extracts at different times after they were shifted to 37° C. and the activity of ILPs in these extracts was monitored by a fluorimetric assay (FIG. 7).

Vanadate prevents the rate of proteolysis from increasing but does not decrease the existing rate. Extracts were incubated at 37° C. and vanadate was added at the indicated times (arrows) to a final concentration of 5 mM. The rate of DEVD-AFC proteolysis in untreated extract (closed symbols) or vanadate treated extracts (open symbols) was measured at the indicated times. Data is representative of three experiments.

Vanadate arrested the process of ILP activation irrespective of when it was added to the extract. One explanation was that rather than blocking activation, vanadate increased the rate of ILP inactivation. However, affinity labeling showed that the pattern of ILPs did not change after addition of vanadate and the processing of cpp32 was frozen at the stage when vanadate was added. Thus it is unlikely that vanadate accelerates ILP inactivation.

Activation of ILPs Requires a Vanadate Sensitive Step.

As a result of our limited screen we found that vanadate blocked ILP activation without blocking activity and showed that activation of ILP in extracts involved a vanadate-sensitive step.

Identifying Drugs That Block ILP Activation.

Inappropriate apoptosis may underlie a number of neurodegenerative diseases and blocking apoptosis would be of value in treating these diseases. Apoptosis involves the activation of multiple ILPs with different substrate specificity and this suggests that, unless a key ILP can be identified, an inhibitor of protease activity will be of little therapeutic use. The effect of vanadate shows for the first time that a low molecular weight compound can block activation of ILPs. This observation will help elucidate the mechanism of activation and the development of anti-apoptotic drugs which target ILP activation rather than ILP activity.

This obviates the need for a drug that blocks multiple protease activities and thus may be a more promising therapeutic approach.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a compound which inhibits apoptosis in transformed mammalian cells, comprising the steps of:
   a) combining
      1) a compound to be assessed; and
      2) a cellular extract obtained from transformed mammalian cells, wherein the cellular extract comprises apoptotic machinery and a pro-apoptotic signal capable of activating the apoptotic machinery, and wherein the apoptotic machinery and the signal are uncoupled; and
   b) maintaining the combination produced in a) under conditions in which the apoptotic machinery is coupled to the signal which allows apoptosis to occur, wherein the conditions do not include addition of an exogenous agent that activates the apoptotic machinery; and
   c) detecting inhibition of apoptosis in the presence of the compound to be assessed, wherein inhibition of apoptosis indicates that the compound to be assessed inhibits apoptosis in transformed cells.

2. The method of claim 1 wherein the signal of a) 2) activates interleukin-1B-converting enzyme-like proteases present in the apoptotic machinery of a) 2).

3. The method of claim 1 wherein the cells are transformed with the oncogene selected from the group consisting of: E1A, E7, c-myc, c-myb, cdc-25, E2A-PBX1 and ras.

4. The method of claim 3 wherein the transformed cells are selected from the group consisting of: 293 cells, HeLa cells, transformed mouse embryo fibroblasts and transformed human fibroblasts.

5. The method of claim 1 wherein the combination is maintained at about 37° C.

6. The method of claim 1 further comprising addition of cell nuclei in step a) wherein apoptosis is detecting by examining the cell nuclei for morphological changes associated with apoptosis.

7. The method of claim 6 wherein the cell nuclei are obtained from cells selected from the group consisting of: HeLa cells, 293 cells, fibroblasts, mouse embryo fibroblasts and Jurkat cells.

8. The method of claim 1 wherein apoptosis is detected by determining interleukin-1B-converting enzyme-like protease activation.

9. The method of claim 8 wherein activation of interleukin-1B-converting enzyme-like proteases is detected using an assay selected from the group consisting of: measuring interleukin-1B-converting enzyme-like protease activity on a fluorogenic substrate, visualizing interleukin-1B-converting enzyme-like protease activity by affinity labeling, and detecting processing of cpp32.

10. A method of identifying a compound which inhibits apoptosis in transformed mammalian cells, comprising the steps of:
   a) combining
      1) a compound to be assessed; and
      2) a cellular extract obtained from 293 cells, wherein the cellular extract comprises apoptotic machinery and a pro-apoptotic signal capable of activating the apoptotic machinery, and wherein the apoptotic machinery and the signal are uncoupled; and
   b) maintaining the combination produced in a) under conditions in which the apoptotic machinery is coupled to the signal which allows apoptosis to occur, wherein the conditions do not include addition of an exogenous agent that activates the apoptotic machinery; and
   c) detecting inhibition of apoptosis in the presence of the compound to be assessed, wherein inhibition of apoptosis indicates that the compound to be assessed inhibits apoptosis in transformed cells.

11. The method of claim 10 wherein the signal of a) 2) activates interleukin-1B-converting enzyme-like proteases present in the apoptotic machinery of a) 2).

12. The method of claim 10 wherein apoptosis is detected by determining interleukin-1B-converting enzyme-like protease activation.

13. The method of claim 10 wherein the combination is maintained at 37° C.

14. The method of claim 10 further comprising addition of cell nuclei in step (a) wherein apoptosis is detected by examining cell nuclei for morphological changes associated with apoptosis.

15. A method of identifying a compound which inhibits apoptosis in transformed mammalian cells, comprising the steps of:
   a) combining
      1) a compound to be assessed; and
      2) a cellular extract obtained from fibroblast cells which express E1A, wherein the cellular extract comprises apoptotic machinery and a pro-apoptotic signal capable of activating the apoptotic machinery, and wherein the apoptotic machinery and the signal are uncoupled; and
   b) maintaining the combination produced in a) under conditions in which the apoptotic machinery is coupled to the signal which allows apoptosis to occur, wherein the conditions do not include addition of an exogenous agent that activates the apoptotic machinery; and
   c) detecting inhibition of apoptosis in the presence of the compound to be assessed, wherein inhibition of apoptosis indicates that the compound to be assessed inhibits apoptosis in transformed cells.

16. The method of claim 15 wherein the signal of a) 2) activates interleukin-1B-converting enzyme-like proteases present in the apoptotic machinery of a) 2).

17. The method of claim 15 wherein apoptosis is detected by determining interleukin-1B-converting enzyme-like protease activation.

18. The method of claim 15 wherein the combination is maintained at 37° C.

19. The method of claim 15 further comprising addition of cell nuclei in step (a) wherein apoptosis is detected by examining cell nuclei for morphological changes associated with apoptosis.

20. The method of claim 16 wherein the fibroblast cells are mouse embryo fibroblast cells.

* * * * *